US012752063B2

(12) United States Patent
Dekalb

(10) Patent No.: US 12,752,063 B2
(45) Date of Patent: Oct. 6, 2026

(54) TRACKING SYSTEM FOR A COUPLING DEVICE

(71) Applicant: CareFusion 303, Inc., San Diego, CA (US)

(72) Inventor: Shawn Wayne Dekalb, Prescott, AZ (US)

(73) Assignee: CAREFUSION 303, INC., San Diego, CA (US)

( * ) Notice: Subject to any disclaimer, the term of this patent is extended or adjusted under 35 U.S.C. 154(b) by 736 days.

(21) Appl. No.: 18/197,644

(22) Filed: May 15, 2023

(65) Prior Publication Data

US 2024/0382694 A1 Nov. 21, 2024

(51) Int. Cl.
*A61M 5/32* (2006.01)

(52) U.S. Cl.
CPC ......... *A61M 5/326* (2013.01); *A61M 2205/33* (2013.01)

(58) Field of Classification Search
CPC .. A61M 2039/1022; A61M 2039/1044; A61M 2039/1066; A61M 5/3243; A61M 5/3257; A61M 5/326; A61M 2005/3267
See application file for complete search history.

(56) References Cited

U.S. PATENT DOCUMENTS

| | | | | |
|---|---|---|---|---|
| 7,976,508 | B2 | 7/2011 | Hoag | |
| 9,999,717 | B2 | 6/2018 | van der Merwe et al. | |
| 10,076,609 | B2 | 9/2018 | Ashby et al. | |
| 2013/0270820 | A1* | 10/2013 | Py | F16L 37/30 285/330 |
| 2014/0276213 | A1 | 9/2014 | Bochenko | |
| 2016/0230914 | A1* | 8/2016 | Roy | A61M 39/00 |
| 2017/0124845 | A1* | 5/2017 | Potyrailo | G06K 19/0707 |
| 2019/0022369 | A1* | 1/2019 | Schultz | A61M 39/162 |
| 2020/0066389 | A1 | 2/2020 | Prince et al. | |
| 2020/0324047 | A1* | 10/2020 | Beggs | A61M 5/16886 |

FOREIGN PATENT DOCUMENTS

| | | | | |
|---|---|---|---|---|
| WO | WO-2010091811 | A1 * | 8/2010 | A61B 90/98 |
| WO | WO-2021037653 | A1 | 3/2021 | |

OTHER PUBLICATIONS

International Search Report and Written Opinion for Application No. PCT/US2024/028395, dated Sep. 19, 2024, 10 pages.

* cited by examiner

*Primary Examiner* — Chelsea E Stinson
*Assistant Examiner* — Eric A Lange
(74) *Attorney, Agent, or Firm* — MASCHOFF BRENNAN

(57) ABSTRACT

A tracking system including a first connector having a needle extending from the first connector and a needle guard circumferentially surrounding the needle, a second connector removably coupled to the first connector, the second connector having an opening configured to receive the needle when the first connector is coupled to the second connector, a wireless transmitter disposed on one of the first connector and the second connector, the wireless transmitter configured to wirelessly communicate with an external device, and a shield coupled to one of the first connector and the second connector, the shield configured to axially move relative to the wireless transmitter to block and unblock the wireless transmitter.

20 Claims, 5 Drawing Sheets

TRACKING SYSTEM FOR A COUPLING DEVICE

FIELD OF THE INVENTION

The present disclosure generally relates to a tracking device, and, in particular, to a tracking system for a coupling device.

BACKGROUND

Medical treatments often include the infusion of a medical fluid (e.g., a saline solution or a liquid medication) to patients using an intravenous (IV) catheter that is connected though an arrangement of flexible tubing and fittings to a source of fluid, for example, an IV bag. Infusion sets are used to deliver medical fluid to patients through the IV catheter. Infusion sets include IV pumps, syringes, and/or NFCs (Needle Free Connectors) used for providing fluid access to the IV catheter or delivery line. NFCs are a common means to dispense fluid and/or drugs rapidly in the middle of treatment to a patient. In some applications, NFCs may be overused, such as repeated use past the lifetime of the NFC, resulting in increased risk of infection, leakage, disconnection, or occlusions.

SUMMARY

One or more embodiments of the present disclosure are directed to a tracking system including a first connector having a needle extending from the first connector and a needle guard circumferentially surrounding the needle, a second connector removably coupled to the first connector, the second connector having an opening configured to receive the needle when the first connector is coupled to the second connector, a wireless transmitter disposed on one of the first connector and the second connector, the wireless transmitter configured to wirelessly communicate with an external device, and a shield coupled to one of the first connector and the second connector, the shield configured to axially move relative to the wireless transmitter to block and unblock the wireless transmitter.

In some embodiments, the shield includes a biasing element having a compressed state and an expanded state, the shield being in a compressed state when the biasing element is in the compressed state and the shield being in an extended state when the biasing element is in the expanded state. The biasing element causes axially movement of the shield relative to the first connector. The biasing element causes axially movement of the shield relative to the second connector.

In some embodiments, the tracking system further includes a tracking device communicatively coupled to the wireless transmitter, wherein the tracking device is configured to transmit a signal to the wireless transmitter and receive a response signal from the wireless transmitter in response to the signal. The tracking device is disposed proximate the wireless transmitter. The tracking device is configured to track a status change of the wireless transmitter. The status change includes one of the wireless transmitter transitioning from a blocked state to an unblocked state and the wireless transmitter transitioning from the unblocked state to the blocked state.

In some embodiments, the tracking system further includes a flow control device coupled to the second connector via a delivery line and configured to control a flow of fluid within the delivery line, the flow control device including a tracking device communicatively coupled to the wireless transmitter. The tracking device is configured to transmit a signal to the wireless transmitter and receive a response signal from the wireless transmitter in response to the signal.

In some embodiments, the shield is coupled to the second connector via a biasing element.

In some embodiments, the shield is coupled to the first connector via a biasing element. The shield includes a leg extending from the shield, the leg and the shield configured to move upon application of a force.

In some embodiments, the shield covers and blocks the wireless transmitter when the first connector is decoupled from the second connector.

In some embodiments, the shield uncovers the wireless transmitter when the first connector is coupled from the second connector. The shield uncovers the wireless transmitter when the first connector is decoupled from the second connector.

In some embodiments, the shield blocks and covers the wireless transmitter when the first connector is coupled from the second connector.

In some embodiments, the shield is coupled to the first connector such that it circumferentially surrounds the needle guard and the needle.

In some embodiments, the shield is coupled to the second connector such that it circumferentially surrounds the opening.

One or more embodiments of the present disclosure are directed to a tracking system including a first connector having a needle extending from the first connector and a needle guard circumferentially surrounding the needle, a second connector removably coupled to the first connector, the second connector having an opening configured to receive the needle when the first connector is coupled to the second connector, a wireless transmitter disposed on one of the first connector and the second connector, the wireless transmitter configured to wirelessly communicate with an external device, a shield coupled to one of the first connector and the second connector, the shield configured to axially move relative to the wireless transmitter to block and unblock the wireless transmitter, and a tracking device communicatively coupled to the wireless transmitter, wherein the tracking device is configured to detect a status change of the wireless transmitter.

One or more embodiments of the present disclosure are directed to a method of tracking a coupling device, the method includes detecting a first status of a wireless transmitter coupled to a coupling device, the first status associated with the coupling device being in an uncoupled configuration and the wireless transmitter being in one of a blocked or an unblocked state, wherein the coupling device includes a first connector coupled to a fluid source and a second connector coupled to a patient, detecting a second status of the wireless transmitter, the second status associated with the coupling device being in a coupled configuration and the wireless transmitter being in the blocked or the unblocked state, wherein the second status is different than the first status, determining a status change of the wireless transmitter when the wireless transmitter transitions the first status to the second status, based on the status change, increase a status change number associated with a total number of status changes detected for the wireless transmitter, compare the status change number to a predetermined threshold, and generate an alert if the status change number exceeds the predetermined threshold.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
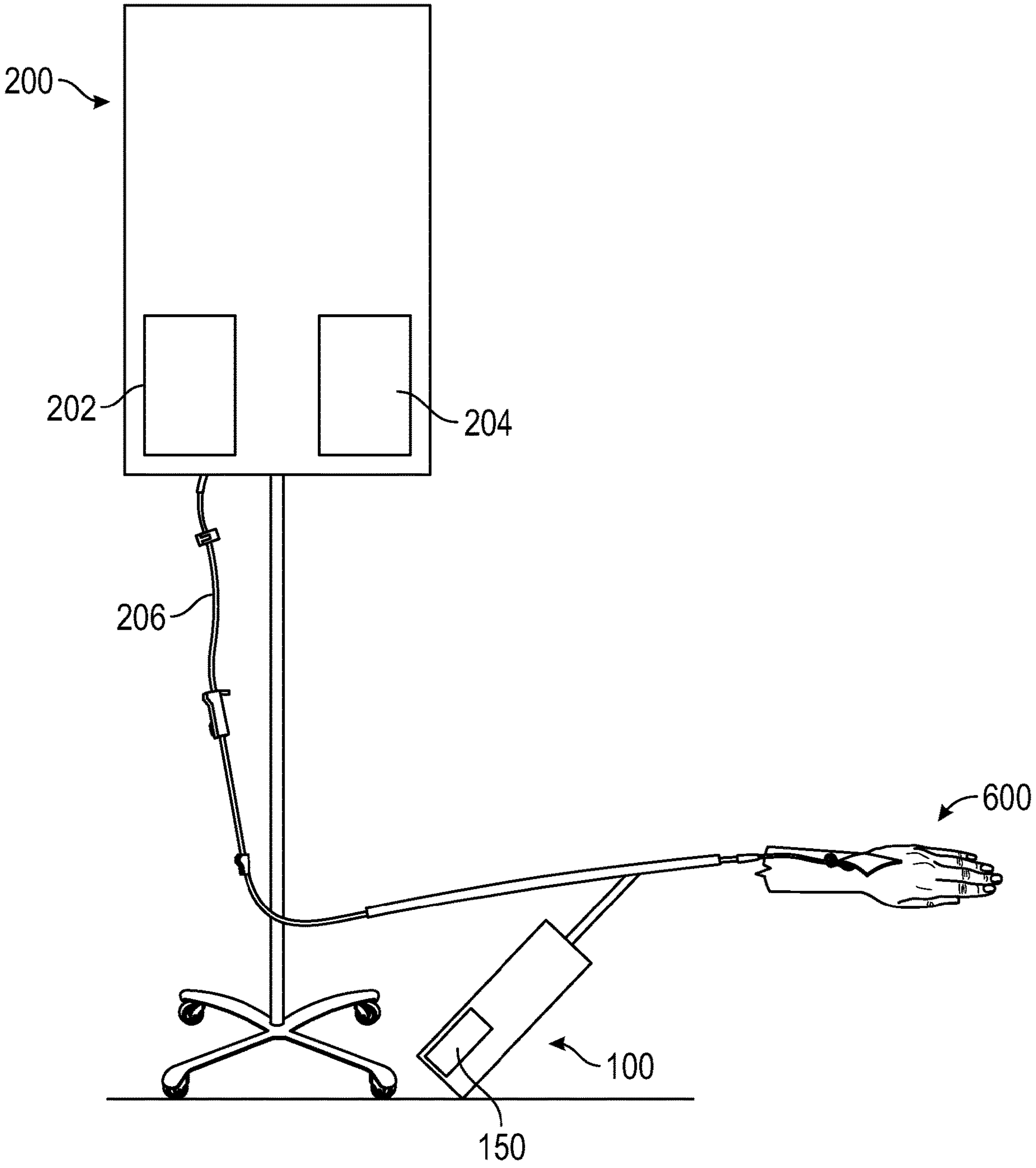
FIG. 1 is a system diagram showing a tracking system for a coupling device in use, in accordance with various aspects of the present disclosure.

The disclosed tracking system includes a coupling device having least two connectors (e.g., a first connector and a second connector) and a tracking device. The two connectors may include a first connector and a second connector. The first connector may be a syringe and the second connector may be a needle free connector (NFC) configured to receive the first connector. However, the two connectors may be any type of connectors. The first connector is coupled to a fluid source and the second connector is coupled to a portion of tubing coupling to a patient. The first connector and the second connector may comprise an infusion set configured to allow for rapid infusion of fluids (e.g., medical fluids) into the patient. The coupling device may have a coupled configuration where the first connector is coupled to the second connector for the delivery of fluids. The coupling device may also have an uncoupled configuration where the first connector is decoupled from the second connector. In some embodiments, the second connector remains coupled to the patient via tubing and the first connector is removable coupled to the second connector.

The coupling device may transition to the coupled configuration for the delivery of fluids. Upon completion of the delivery of fluids, the coupling device may transition to the uncoupled configuration. The coupling device may remain in the uncoupled configuration (e.g., the first connector decoupled from the second connector) until another dose or fluid is required, which then the coupling device transitions to the coupled configuration such that the first connector is coupled to the second connector to deliver the medical fluid to the patient.

The coupling device may be controlled by a flow control device (e.g., a pump). The flow control device is configured to control the flow of medical fluid to the patient. The flow control device is coupled to the second connector via one or more tubings to control the flow of fluid from the second connector to the patient. For example, a user may deliver medical fluids to a patient via the second connector and the flow control device may control the flow (e.g., flow rate) of the fluid to the patient. In some embodiments, the second connector is coupled to another delivery line (e.g., tube) allowing for the infusion of medical fluid into the delivery line and to the patient. The flow control device may control the flow of fluids through the delivery line.

The coupling device includes a tracking system configured to track or monitor the number of times second connector is used to delivery medical fluids to the patient. For example, the tracking system is configured to track the number of times coupling device enters the coupled configuration indicating the number of times that the first connector couples to the second connector to deliver medical fluids. Tracking or monitoring the transitions of coupling device from the coupled configuration to the uncoupled configuration allows for monitoring the usage of coupling device. For example, each time that coupling device transitions from the uncoupled configuration to the coupled configuration indicates use of the second connector and delivery of medical fluid. Overuse of the second connector can result in degradation of the second connector and can lead to leakage, infection, occlusions, or disconnections.

The tracking system includes a wireless transmitter coupled to coupling device, such as to the first connector and/or the second connector. In some embodiments, the wireless transmitter is a radio frequency identification (RFID) tag or transmitter. The wireless transmitter may be configured to be in communication with the flow control device. In some embodiments, when the wireless transmitter is proximate the flow control device, the flow control device is able to track and monitor the usage of the coupling device.

The coupling device may include a shroud configured to block and unblock signal from wireless transmitter. In some embodiments, when coupling device is in the coupled configuration, the shroud unblocks signal from the wireless transmitter allowing it to communicate with the flow control device. Alternatively, when coupling device is in the uncoupled configuration, the shroud unblocks signal from the wireless transmitter allowing it to communicate with the flow control device. The shroud is configured to block and unblock the wireless transmitter during transition of the coupling device from the coupled configuration to the uncoupled configuration. For example, coupling first connector to the second connector may result in shroud unblocking the wireless transmitter. In some embodiments, coupling first connector to the second connector may result in shroud blocking the wireless transmitter.

The flow control device may be configured to monitor a change in status (e.g., blocked to unblocked or unblocked to blocked) of the wireless transmitter to track the usage of coupling device. In some embodiments, the flow control device includes a counter configured to count the changes in the status of coupling device. When the number of changes in the status of coupling device exceeds a predetermined threshold, the flow control device transmits an alarm to indicate that second connector needs to be replaced due to over usage or usage beyond its shelf life. The second connector may be replaced resulting in a new wireless transmitter and a resetting of the counter of the flow control device.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the tracking system for medical connectors, it is to be understood that this description is only an example of usage and does not limit the scope of the claims. Various aspects of the disclosed tracking system may be used in any application where it is desirable to track the usage of medical connectors or couplers.

The disclosed tracking system and coupler overcomes several challenges discovered with respect to certain conventional coupling devices. One challenge with certain conventional couplers is that certain conventional couplers may be overused or used beyond their shelf life. For example, certain conventional couplers may be used beyond their shelf life resulting in malfunction of the coupler. This can result in infection, occlusions, disconnectors, or other issues.

Therefore, in accordance with the present disclosure, it is advantageous to provide couplers and coupler/connector assemblies as described herein that allows for improved securement of fittings or connectors. The disclosed couplers and coupler/connector assemblies are structured as described herein so as to permit the secure retention of the first connectors, while allowing for decoupling after a disconnection event.

FIG. 1 is a system diagram showing a tracking system for a coupling device in use, in accordance with various aspects of the present disclosure.

With reference to FIG. 1, coupler device 100 allows for the infusion of fluid, such as a medical fluid, to the patient. Coupling device 100 may include first connector 102 and second connector 120. Second connector 120 may be coupled to a fluid line (e.g., tubing) that is coupled to a patient. First connector 102 may be coupled to removably couple to second connector 120 to deliver fluid to second connector 120. First connector 102 may be a syringe couple to or include fluid to be delivered to the patient. Second connector 120 may be a needless fluid connector (NFC) configured to receive and couple to first connector 102. Upon coupling of first connector 102 to second connector 120, fluid may flow from the first connector 102 to second connector 120 and to the patient via a portion of tubing. In some embodiments, the fluid flows from the first connector 102 to second connector 120 to a delivery line coupling the patient to fluid control device 200. For example, a delivery line may be coupled to the patient via a catheter on one end and coupled to fluid control device 200 at another end. The delivery line may include a Y-connector coupled to second connector 120 to allow for the infusion of fluid from first connector 102 to the delivery line via second connector 120.

Fluid control device 200 may be configured to control the flow of fluid within the delivery line. In some embodiments, fluid control device 200 is a pump configured to control the flow of fluid to the patient. For example, fluid control device 200 may include fluid source 204, which may be coupled to the patient via delivery line 206. Delivery line 206 may couple fluid source 204 to the patient and may include one or more branches. In some embodiments, one of the branches is coupled to coupling device 100 (e.g., second connector 120). In some embodiments, first connector 102 may be coupled to a fluid source coupled to or disposed within fluid control device 200.

Fluid control device 200 may include tracking device 202. Tracking device 202 may include a reading device and may be configured communicate with a transmitter (e.g., wireless transmitter 150) disposed on or coupled to coupling device 100. In some embodiments tracking device 202 is configured to monitor and track/count the status changes of transmitter 150. For example, tracking device 202 may be in communication with transmitter 150 and may count the change in status (e.g., blocked, unblocked) of the transmitter. Tracking device 202 may be configured to monitor the usage of coupling device 100. The usage of coupling device 100 may include the number of times coupling device 100 goes from the uncoupled position to the coupled position.

Transition of coupling device 100 from the uncoupled position to the coupled position may result in a change in status of transmitter 150. In some embodiments, transition of coupling device 100 is due to actuation of coupling device 100 (e.g., coupling of first connector 102 to second connector 120). Usage of coupling device 100, such as second connector 120, over the shelf-life may result in malfunction of coupling device 100 resulting in infection, occlusions, disconnections, or other issues with coupling device 100. The usage may be tracked from the first use of coupling device 100 such that the total number of uses of coupling device 100 is tracked and counted by tracking device 202.

In some embodiments, the change in status of transmitter 150 of coupling device 100 corresponds to change in configuration of coupling device 100. For example, coupling device 100 going from the uncoupled configuration to the coupled configuration may result in a change in the status of transmitter 150 of coupling device 100. Tracking device 202 may be configured to transmit an alarm or indicator when the count in the change of status of transmitter 150 exceeds a predetermined threshold. For example, when tracking device 202 determines that the number of changes of the status of transmitter 150 exceeds a predetermined threshold, tracking device 202 may transmit an alarm, indication, or notification to notify a medical professional that the shelf-life of coupling device 100 (e.g., second connector 120) has expired or that coupling device 100 has been used the allotted number of times.

In some embodiments, depending on the state of transmitter 150 when coupling device 100 is in the uncoupled configuration, tracking device 202 increases an internal counter in response to a specific status change. For example, if transmitter 150 is covered or blocked when coupling device 100 is in the uncoupled configuration, tracking device 202 may only track or count status changes when transmitter 150 transitions from being blocked to unblocked. Further, if transmitter 150 is unblocked when coupling device 100 is in the uncoupled configuration, tracking device 202 may only track or count status changes when transmitter 150 transitions from being unblocked to blocked.

Once the internal counter reaches the predetermined threshold limit, tracking device 202 may transmit an alarm, indication, or notification to alert a medical professional that coupling device 100 needs to be replaced. Replacing of coupling device 100 results in the replacing of transmitter 150 thereby resetting the count of tracking device 202. The predetermined threshold may be 5 uses to 100 uses, 10 uses to 90 uses, 15 uses to 75 uses, 25 uses to 50 uses, or greater than 100 uses.

In some embodiments, transmitter 150 is coupled to or disposed on coupling device 100. For example, coupling device 100 may include first connector 102 and second connector 120, and transmitter 150 may be disposed on either first connector 102 or second connector 120. In some embodiments, transmitter 150 is a wireless transmitter such as an RFID device.

Transmitter 150 may be configured to store information associated with coupling device 100. For example, transmitter 150 may store the serial number, date of manufacture, expiration or shelf-life date, number of allotted actuations of coupling device 100, manufacturer, size, product type, or any other information associated with coupling device 100.

Transmitter 150 may be in wireless communication with fluid control device 200 (e.g., tracking device 202). Transmitter 150 may allow for passive communication with tracking device 202. For example, transmitter 150 may not require a power source and tracking device 202 may transmit radio waves to transmitter 150 to power transmitter 150 to allow transmitter 150 to transmit that status (blocked or unblocked) to tracking device 202. In some embodiments, use (e.g., actuation) of coupling device 100 results in transmitter 150 being proximate to tracking device 202 such that transmitter 150 is continuously transmitting a signal to tracking device 202. Transmitter 150 may be blocked resulting in transmitter 150 no longer transmitting the signal to tracking device 202. Upon unblocking of transmitter 150, transmitter 150 may continue to communicate with tracking device 202. Transmitter 150 may be blocked or unblocked due to coupling and uncoupling of first connector 102 and second connector 120.

Tracking device 202 is configured to detect the status change of transmitter 150, which is caused by actuation of coupling device 100. For example, coupling device 100 may be configured to block and unblock transmitter 150 based on the configuration of coupling device 100. In some embodiments, coupling device 100 being in the coupled configuration results in transmitter 150 being unblocked. In other embodiments, coupling device 100 being in the coupled configuration results in transmitter 150 being blocked. When transmitter 150 is blocked, tracking device 202 is no longer able to receive a signal from transmitter 150. Upon unblocking of transmitter 150, tracking device 202 may receive a signal from transmitter 150.

In some embodiments, tracking device 202 continuously sends a signal to transmitter 150, which receives the signal and transmits a response signal. The signal from tracking device 202 to transmitter 150 may provide power to transmitter 150 allowing it to transmit a response signal. In some embodiments, transmitter 150 is coupled to a power source and transmits the response signal upon receipt of the signal from tracking device 202.

Tracking device 202 may be configured to count the changes of transmitter 150 from blocked to unblocked or blocked to unblocked to determine each use or actuation of coupling device 100. For example, each a status change of transmitter 150 based on whether tracking device 202 receives a signal from transmitter 150 indicates an actuation of coupling device 100. Each actuation of coupling device 100 increases a counter of tracking device 202 such that tracking device 202 can count each use of second connector 102 of coupling device 100.

Based on the location of transmitter 150 and the presence of a blocking element (e.g., shield 130), tracking device 202 may be configured to only track and count one-way status changes. For example, tracking device 202 may be configured to only track and count when transmitter 150 transitions from being blocked to unblocked, but not unblocked to blocked. Transmitter 150 may be blocked based on a shroud or shield disposed on coupling device 100. For example, first connector 102 and/or second connector 120 may include a shroud or shield (e.g., shield 130) configured to block signals to and from transmitter 150. The shroud or shield may cover transmitter 150 such that signal to and from transmitter 150 are blocked. Movement of the shroud or shield such that transmitter 150 is no longer covered results in transmitter 150 being able to receive and transmit signals, such as to tracking device 202.

In some embodiments, when transmitter 150 is blocked when coupling device 100 is in the uncoupled configuration, tracking device 202 only tracks when transmitter 150 transitions from being blocked to unblocked. In other embodiments, when transmitter 150 is unblocked when coupling device 100 is in the uncoupled configuration, tracking device 202 only tracks when transmitter 150 transitions from being unblocked to blocked.

Figure 2A:
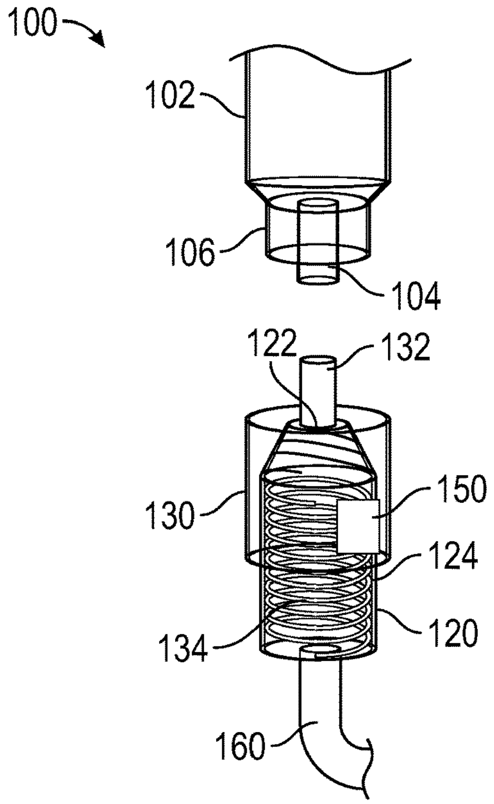
FIG. 2A is a front view of a first embodiment of the tracking system of FIG. 1 with the coupling device in an uncoupled configuration, in accordance with various aspects of the present disclosure.
Figure 2B:
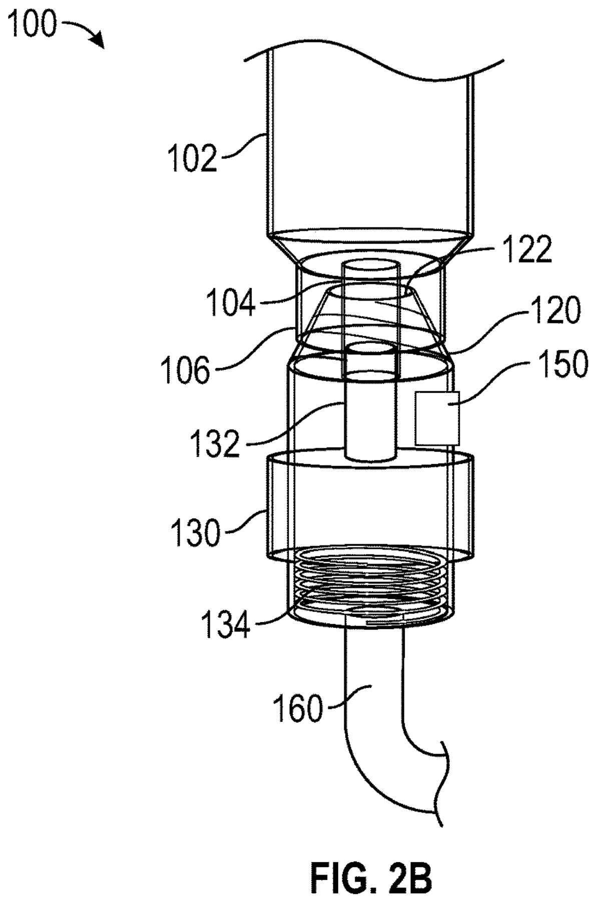
FIG. 2B is a front view of the tracking system of FIG. 2A with the coupling device in a coupled configuration, in accordance with various aspects of the present disclosure.

FIG. 2A is a front view of a first embodiment of the tracking system of FIG. 1 with the coupling device in an uncoupled configuration, in accordance with various aspects of the present disclosure. FIG. 2B is a front view of the tracking system of FIG. 2A with the coupling device in a coupled configuration, in accordance with various aspects of the present disclosure.

Referring to FIGS. 2A-2B, there is shown a first embodiment of coupling device 100. Coupling device 100 may include first connector 102 and second connector 120. First connector 102 may be removably coupled to second connector 120. Second connector 120 may be coupled to tube 160, which may be coupled to a patient. First connector 102 may include a fluid source or be coupled to a fluid source and may be configured to deliver fluid from the fluid source to tube 160 via second connector 120. Coupling device 100 may be in the uncoupled configuration (FIG. 2A) where first connector 102 is uncoupled from second connector 120 and in the coupled configuration (FIG. 2B) where first connector 102 is coupled to second connector 120.

First connector 102 may be a syringe and may include needle 104 and needle guard 106. Needle guard 106 may be disposed around needle 104 and may be configured to protect needle 104. In some embodiments, needle guard 106 circumferentially surrounds needle 104. Second connector 120 may include opening 122 configured to receive needle 104 during coupling of first connector 102 to second connector 120 (e.g., coupling device 100 being in the coupled configuration). Second connector 120 may include body 124 disposed between tube 160 and opening 122. Opening 122 may be disposed opposite tube 160.

In some embodiments, second connector 120 includes shield 130 disposed at least partially around second connector 120. For example, shield 130 may be disposed around opening 122. Shield 130 may include leg 132 and biasing element 134. Leg 132 may extend from shield 130 away from tube 160. For example, leg 132 may be disposed proximate opening 122 and may extend away from shield 130 such that it extends away from tube 160. Shield 130 may be coupled to second connector 120 via biasing element 134. Shield 130 may be configured to axially move relative to second connector 120. For example, shield 130 may be coupled to second connector 120 via biasing element 134 and may be configured to axially move relative to second connector 120 due to biasing element 134. Biasing element 134 may be biased in an expanded state such that shield 130 at least partially surrounds opening 122. Biasing element 134 may be coupled to shield 130 and disposed opposite leg 132. Biasing element 134 may be configured to couple shield 130 to body 124 of first connector 102. In some embodiments, leg 132 is disposed proximate opening 122 compared to biasing element 134.

Biasing element 134 may be configured to transition from the expanded state to the compressed state in response to a force. Shield 130 may be in an extended state when biasing element 134 is in the expanded state and may be in the compressed state when biasing element 134 is in the compressed state. In the compressed state, shield 130 may be disposed proximate tube 160 and around body 124. In some embodiments, shield 130 is proximate opening 122 when biasing element 134 is in the expanded state compared to when biasing element 134 is in the compressed state. Further, shield 130 may be proximate tube 160 when biasing element 134 is in the compressed state compared to when biasing element 134 is in the expanded state.

Second connector 120 may include transmitter 150 such that transmitter 150 is disposed on second connector 120. In some embodiments, shield 130 covers transmitter 150 when shield 130 is in the extended state due to biasing element 134 being in the expanded state. When shield 130 is in the extended state and covers transmitter 150 (FIG. 2B), transmitter 150 is blocked and cannot communicate with tracking device 202. When shield 130 is in the compressed state, transmitter 150 is no longer blocked by shield 130 and can communicate with tracking device 202. Shield 130 moving from the extended state to the compressed state results in a status change of transmitter 150, which is monitored by tracking device 202. In some embodiments, shield 130 is configured to axially move relative to transmitter 150.

As illustrated in FIG. 2A, coupling device 100 may be in the uncoupled configuration such that first connector 102 is decoupled from the second connector 120 and transmitter 150 is blocked by shield 130. Referring to FIG. 2B, upon coupling of first connector 102 to second connector 120, needle guard 106 applies a force to leg 132 pushing leg 132 and shield 130 from the extending state to the compressed state. Further, securing of needle 104 within opening 122 results in needle guard 106 applying a force to leg 132 resulting in biasing element 134 transitioning to the compressed state, which results in shield 130 being in the compressed state. Shield 130 being in the compressed state due to the coupling of first connector 102 to second connector 120 results in transmitter 150 undergoing a status change from being blocked to unblocked and communicating with tracking device 202. The status change is tracked by tracking device 202. In some embodiments, tracking device 202 is configured to only track when transmitter 150 goes from blocked to unblocked thereby preventing tracking and counting of decoupling events.

Figure 3A:
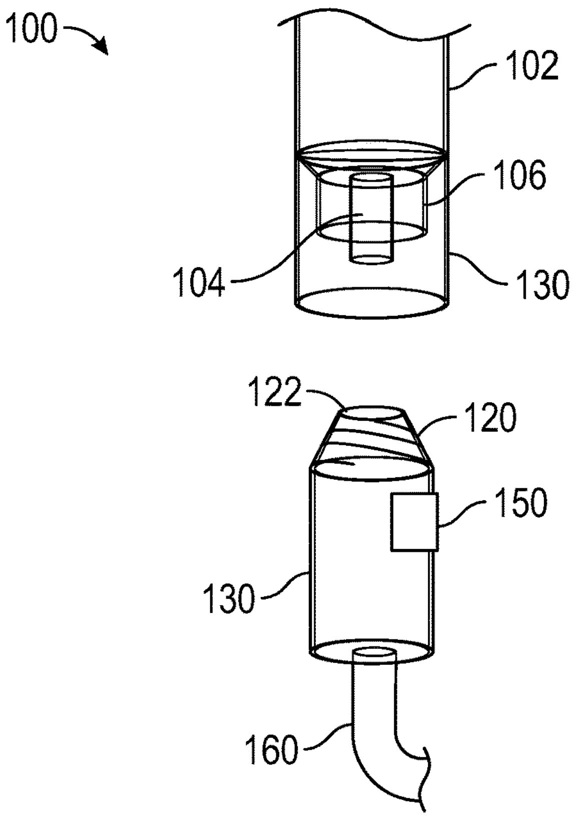
FIG. 3A is a front view of a second embodiment of the tracking system of FIG. 1 with the coupling device in an uncoupled configuration, in accordance with various aspects of the present disclosure.
Figure 3B:
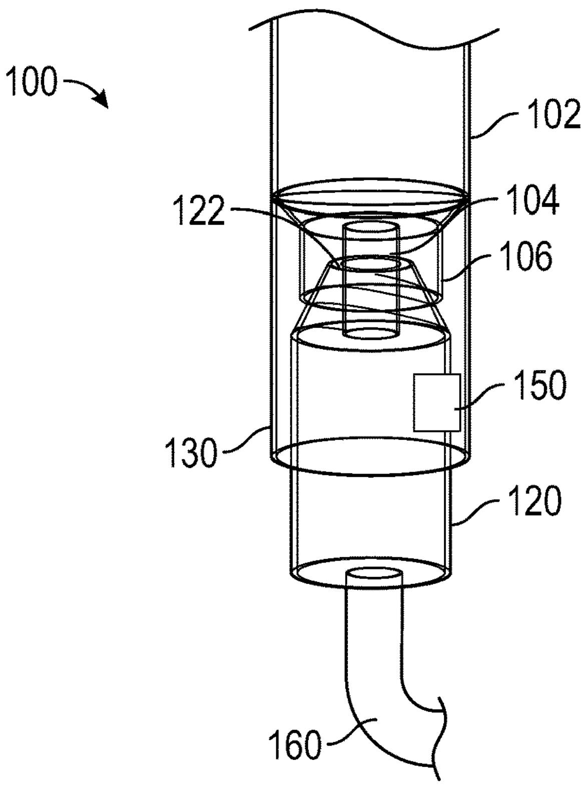
FIG. 3B is a front view of the tracking system of FIG. 3A with the coupling device in a coupled configuration, in accordance with various aspects of the present disclosure.

FIG. 3A is a front view of a second embodiment of the tracking system of FIG. 1 with the coupling device in an uncoupled configuration, in accordance with various aspects of the present disclosure. FIG. 3B is a front view of the tracking system of FIG. 3A with the coupling device in a coupled configuration, in accordance with various aspects of the present disclosure.

Referring to FIGS. 3A-3B, there is shown a second embodiment of coupling device 100. Coupling device 100 may be in the uncoupled configuration (FIG. 3A) where first connector 102 is uncoupled from second connector 120 and in the coupled configuration (FIG. 3B) where first connector 102 is coupled to second connector 120.

First connector 102 may be a syringe and may include needle 104, needle guard 106, and shield 130. Needle guard 106 may be disposed around needle 104 and may be configured to protect needle 104. In some embodiments, needle guard 106 circumferentially surrounds needle 104. Shield 130 may be disposed around needle guard 106 and be configured to extend away from first connector 102. In some embodiments, shield 130 extends beyond needle guard 106. Second connector 120 may include opening 122 configured to receive needle 104 during coupling of first connector 102 to second connector 120 (e.g., coupling device 100 being in the coupled configuration). Second connector 120 may include transmitter 150 such that transmitter 150 is disposed on second connector 120.

In some embodiments, first connector 102 being uncoupled from second connector 120 (FIG. 3A) results in transmitter 150 being uncovered and unblocked. Coupling of first connector 102 to second connector 120 results in shield 130 covering and blocking transmitter 150 (FIG. 3B). Shield 130 covering and blocking transmitter 150 due to the coupling of first connector 102 to second connector 120 results in transmitter 150 undergoing a status change from being unblocked to blocked and no longer communicating with tracking device 202. The status change is tracked by tracking device 202. In some embodiments, tracking device 202 is configured to only track when transmitter 150 goes from unblocked to blocked. In some embodiments, shield 130 is configured to axially move relative to transmitter 150.

Figure 4A:
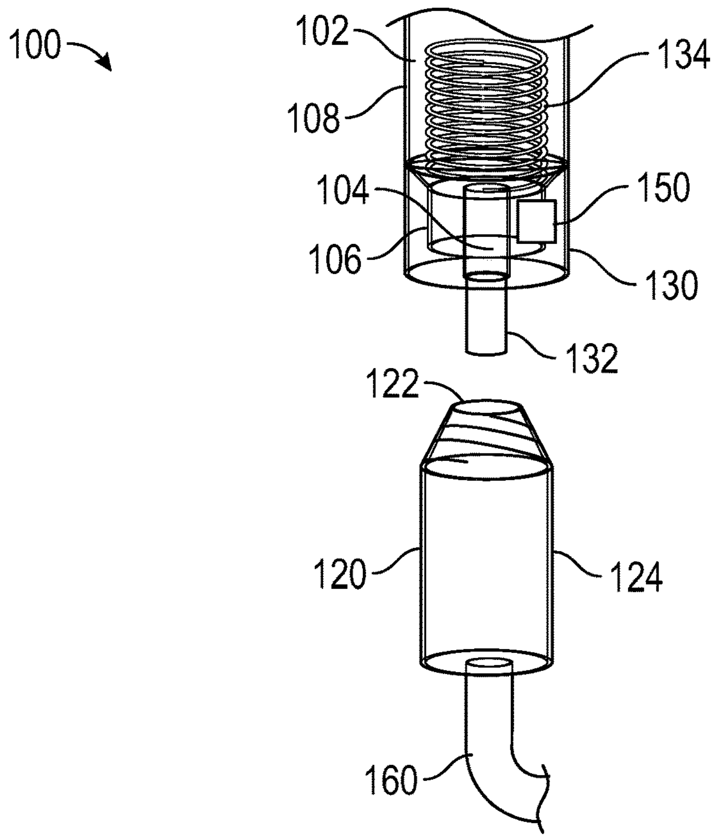
FIG. 4A is a front view of a third embodiment of the tracking system of FIG. 1 with the coupling device in an uncoupled configuration, in accordance with various aspects of the present disclosure.
Figure 4B:
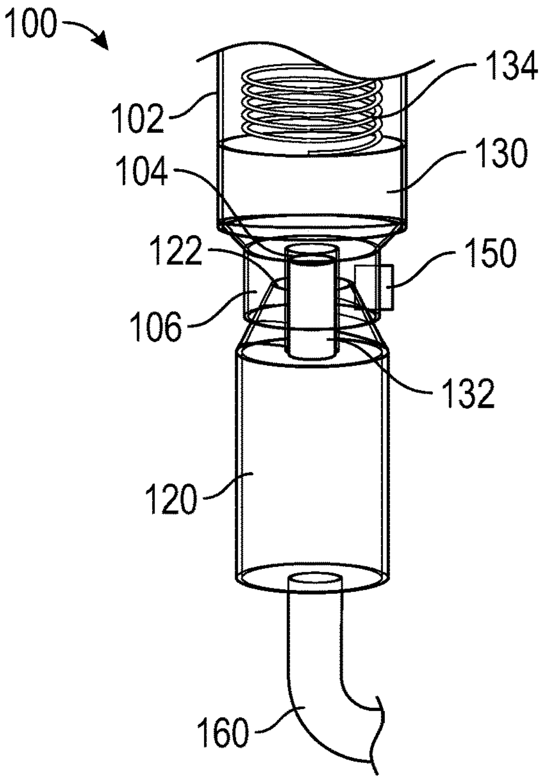
FIG. 4B is a front view of the tracking system of FIG. 4A with the coupling device in a coupled configuration, in accordance with various aspects of the present disclosure.

FIG. 4A is a front view of a third embodiment of the tracking system of FIG. 1 with the coupling device in an uncoupled configuration, in accordance with various aspects of the present disclosure. FIG. 4B is a front view of the tracking system of FIG. 4A with the coupling device in a coupled configuration, in accordance with various aspects of the present disclosure.

Referring to FIGS. 4A-4B, there is shown a third embodiment of coupling device 100. Coupling device 100 may include first connector 102 and second connector 120. Coupling device 100 may be in the uncoupled configuration (FIG. 4A) where first connector 102 is uncoupled from second connector 120 and in the coupled configuration (FIG. 4B) where first connector 102 is coupled to second connector 120.

First connector 102 may be a syringe and may include needle 104, needle guard 106, body 108, and shield 130. Needle 104 and needle guard 106 may extend from body 108. Needle guard 106 may be disposed around needle 104 and may be configured to protect needle 104. In some embodiments, needle guard 106 circumferentially surrounds needle 104. Second connector 120 may include opening 122 configured to receive needle 104 during coupling of first connector 102 to second connector 120 (e.g., coupling device 100 being in the coupled configuration). Second connector 120 may include body 124 disposed between tube 160 and opening 122. Opening 122 may be disposed opposite tube 160.

In some embodiments, first connector 102 includes shield 130 disposed at least partially around first connector 102. For example, shield 130 may be disposed around needle 104 and needle guard 106. Shield 130 may include leg 132 and biasing element 134. Leg 132 may be proximate needle 104 and may extend from shield 130. Shield 130 may be coupled to first connector 102 via biasing element 134. Shield 130 may be configured to axially move relative to first connector 102. For example, shield 130 may be coupled to first connector 102 via biasing element 134 and may be configured to axially move relative to first connector 102 due to biasing element 134. Biasing element 134 may be biased in an expanded state such that shield 130 at least partially surrounds needle 104 and needle guard 106. Biasing element 134 may be coupled to shield 130 and disposed opposite leg 132. Biasing element 134 may be configured to couple shield 130 to body 108 of first connector 102. In some embodiments, leg 132 is disposed proximate needle 104 and needle guard 106 compared to biasing element 134.

Biasing element 134 may be configured to transition from the expanded state to the compressed state in response to a force. Shield 130 may be in an extended state when biasing element 134 is in the expanded state and may be in the compressed state when biasing element 134 is in the compressed state. In the compressed state, shield 130 may be disposed proximate needle 104 and around body 108. In some embodiments, shield 130 is disposed around needle 104 when biasing element 134 is in the expanded state compared to when biasing element 134 is in the compressed state.

First connector 102 may include transmitter 150 such that transmitter 150 is disposed on first connector 102. In some embodiments, shield 130 covers transmitter 150 when shield 130 is in the extended state due to biasing element 134 being in the expanded state. When shield 130 is in the extended state and covers transmitter 150 (FIG. 4A), transmitter 150 is blocked and cannot communicate with tracking device 202. When shield 130 is in the compressed state, transmitter 150 is no longer blocked by shield 130 and can communicate with tracking device 202. Shield 130 moving from the extended state to the compressed state results in a status change of transmitter 150, which is monitored by tracking device 202. In some embodiments, shield 130 is configured to axially move relative to transmitter 150.

As illustrated in FIG. 4A, coupling device 100 may be in the uncoupled configuration such that first connector 102 is decoupled from the second connector 120 and transmitter 150 is blocked by shield 130. Referring to FIG. 4B, upon coupling of first connector 102 to second connector 120, second connector 120 applies a force to leg 132 pushing leg 132 and shield 130 from the extending state to the compressed state. Further, securing of needle 104 within opening 122 results in second connector 102 applying a force to leg 132 resulting in biasing element 134 transitioning to the compressed state, which results in shield 130 being in the compressed state. Shield 130 being in the compressed state due to the coupling of first connector 102 to second connector 120 results in transmitter 150 undergoing a status change from being blocked to unblocked and communicating with tracking device 202. The status change is tracked by tracking device 202. In some embodiments, tracking device 202 is configured to only track when transmitter 150 goes from blocked to unblocked thereby preventing tracking and counting of decoupling events.

Figure 5A:
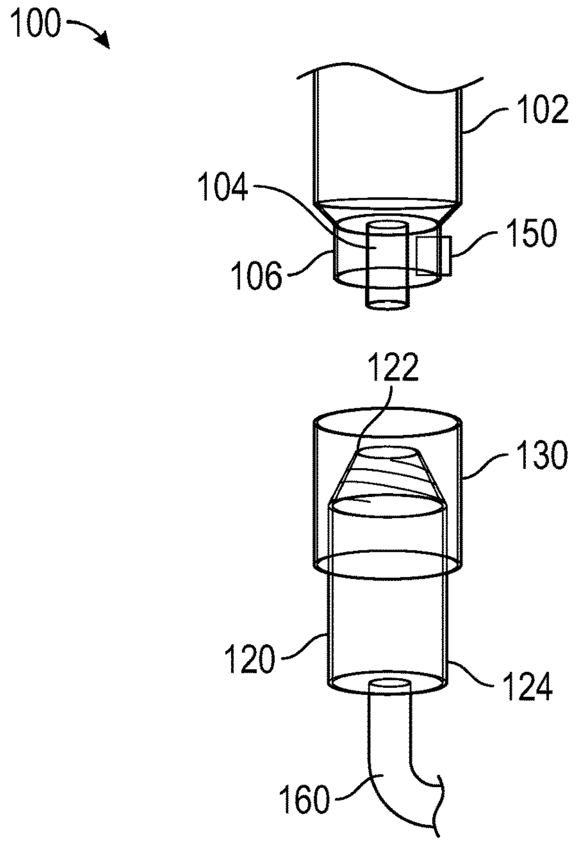
FIG. 5A is a front view of a fourth embodiment of the tracking system of FIG. 1 with the coupling device in an uncoupled configuration, in accordance with various aspects of the present disclosure.
Figure 5B:
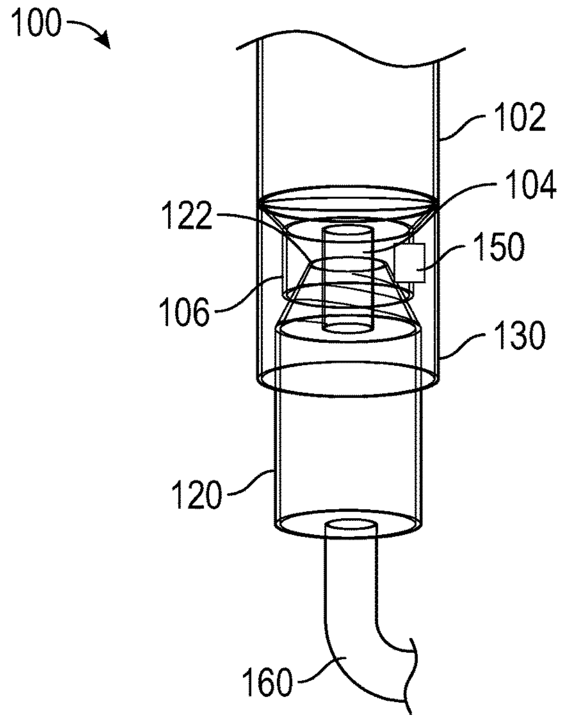
FIG. 5B is a front view of the tracking system of FIG. 5A with the coupling device in a coupled configuration, in accordance with various aspects of the present disclosure.

FIG. 5A is a front view of a fourth embodiment of the tracking system of FIG. 1 with the coupling device in an uncoupled configuration, in accordance with various aspects of the present disclosure. FIG. 5B is a front view of the tracking system of FIG. 5A with the coupling device in a coupled configuration, in accordance with various aspects of the present disclosure.

Referring to FIGS. 5A-5B, there is shown a fourth embodiment of coupling device 100. Coupling device 100 may be in the uncoupled configuration (FIG. 5A) where first connector 102 is uncoupled from second connector 120 and in the coupled configuration (FIG. 5B) where first connector 102 is coupled to second connector 120.

First connector 102 may be a syringe and may include needle 104, needle guard 106, and transmitter 150. Needle guard 106 may be disposed around needle 104 and may be configured to protect needle 104. In some embodiments, needle guard 106 circumferentially surrounds needle 104. First connector 102 may include transmitter 150 such that transmitter 150 is disposed on first connector 102. Second connector 120 may include opening 122 configured to receive needle 104 during coupling of first connector 102 to second connector 120 (e.g., coupling device 100 being in the coupled configuration). In some embodiments, second connector 120 includes shield 130. Shield 130 may be disposed at least partially around body 124. In some embodiments, shield 130 is disposed around opening 122. In some embodiments, shield 130 is configured to axially move relative to transmitter 150.

In some embodiments, first connector 102 being uncoupled from second connector 120 (FIG. 5A) results in transmitter 150 being uncovered and unblocked. Coupling of first connector 102 to second connector 120 results in shield 130 covering and blocking transmitter 150 (FIG. 5B). Shield 130 covering and blocking transmitter 150 due to the coupling of first connector 102 to second connector 120 results in transmitter 150 undergoing a status change from being unblocked to blocked and no longer communicating with tracking device 202. The status change is tracked by tracking device 202. In some embodiments, tracking device 202 is configured to only track when transmitter 150 goes from unblocked to blocked.

In some embodiments, the present disclosure includes a method of tracking a coupling device. In some embodiments, the method is carried out by tracking device 202 and/or fluid control device 200. The method may include detecting a first status of transmitter 150, which may be coupled to coupling device 100. The first status may be associated with coupling device 100 being in an uncoupled configuration and transmitter 150 being in one of a blocked or an unblocked state. For example, coupling device 100 being in an uncoupled configuration may result in coupling device 100 being blocked (FIGS. 2A and 4A) or being unblocked (FIGS. 3A and 5A). The method may include detecting a second status of transmitter 150. The second status may be associated with coupling device 100 being in a coupled configuration and transmitter 150 being in the blocked or the unblocked state. For example, coupling device 100 being in a coupled configuration may result in coupling device 100 being unblocked (FIGS. 2B and 4B) or being blocked (FIGS. 3B and 5B). In some embodiments, the second status is different than the first status.

The method may further include determining a status change of transmitter 150 when transmitter 150 transitions the first status to the second status. The status change of transmitter 150 may be when transmitter 150 transitions from being blocked to unblocked or unblocked to block. The status change may occur due to shield 130 blocking or unblocking transmitter 150 during coupling of first connector 102 to second connector 120. Tracking device 202 may be configured to increase a status change number associated with a total number of status changes detected for transmitter 150. For example, based on a detected status change, tracking device 202 may increase an internal counter by one to indicate that there has been another status change.

The status change may only be tracked based on a specific transition of transmitter 150 based on the state of transmitter 150 when coupling device 100 is in the uncoupled configuration. For example, if transmitter 150 is covered or blocked when coupling device 100 is in the uncoupled configuration, tracking device 202 may only track or count status changes when transmitter 150 transitions from being blocked to unblocked. Further, if transmitter 150 is unblocked when coupling device 100 is in the uncoupled configuration, tracking device 202 may only track or count status changes when transmitter 150 transitions from being unblocked to blocked.

Tracking device 202 may be configured to compare the status change number to a predetermined threshold and transmit a notification if the status change number exceeds the predetermined threshold. For example, if the number of status changes counted or tracked by tracking device 202 exceeds a predetermined threshold, tracking device 202 may transmit or generate an alert, alarm, or notification. The predetermined threshold hold may be associated with a shelf-life or life of coupling device 100, such as second connector 120.

The disclosures described herein include at least the following clauses:

Clause 1: A tracking system including a first connector having a needle extending from the first connector and a needle guard circumferentially surrounding the needle, a second connector removably coupled to the first connector, the second connector having an opening configured to receive the needle when the first connector is coupled to the second connector, a wireless transmitter disposed on one of the first connector and the second connector, the wireless transmitter configured to wirelessly communicate with an external device, and a shield coupled to one of the first connector and the second connector, the shield configured to axially move relative to the wireless transmitter to block and unblock the wireless transmitter.

Clause 2: The tracking system of clause 1, wherein the shield includes a biasing element having a compressed state and an expanded state, the shield being in a compressed state when the biasing element is in the compressed state and the shield being in an extended state when the biasing element is in the expanded state.

Clause 3: The tracking system of clause 2, wherein the biasing element causes axially movement of the shield relative to the first connector.

Clause 4: The tracking system of clause 2, wherein the biasing element causes axially movement of the shield relative to the second connector.

Clause 5: The tracking system of clause 1 further including a tracking device communicatively coupled to the wireless transmitter, wherein the tracking device is configured to transmit a signal to the wireless transmitter and receive a response signal from the wireless transmitter in response to the signal.

Clause 6: The tracking system of clause 5, wherein the tracking device is disposed proximate the wireless transmitter.

Clause 7: The tracking system of clause 5, wherein the tracking device is configured to track a status change of the wireless transmitter.

Clause 8: The tracking system of clause 7, wherein the status change includes one of the wireless transmitter transitioning from a blocked state to an unblocked state and the wireless transmitter transitioning from the unblocked state to the blocked state.

Clause 9: The tracking system of clause 1 further comprising:

a flow control device coupled to the second connector via a delivery line and configured to control a flow of fluid within the delivery line, the flow control device including a tracking device communicatively coupled to the wireless transmitter, wherein the tracking device is configured to transmit a signal to the wireless transmitter and receive a response signal from the wireless transmitter in response to the signal.

Clause 10: The tracking system of clause 1, wherein the shield is coupled to the second connector via a biasing element.

Clause 11: The tracking system of clause 1, wherein the shield is coupled to the first connector via a biasing element.

Clause 12: The tracking system of clause 1, wherein the shield includes a leg extending from the shield, the leg and the shield configured to move upon application of a force.

Clause 13: The tracking system of clause 1, wherein the shield covers and blocks the wireless transmitter when the first connector is decoupled from the second connector.

Clause 14: The tracking system of clause 1, wherein the shield uncovers the wireless transmitter when the first connector is coupled from the second connector.

Clause 15: The tracking system of clause 1, wherein the shield uncovers the wireless transmitter when the first connector is decoupled from the second connector.

Clause 16: The tracking system of clause 1, wherein the shield blocks and covers the wireless transmitter when the first connector is coupled from the second connector.

Clause 17: The tracking system of clause 1, wherein the shield is coupled to the first connector such that it circumferentially surrounds the needle guard and the needle.

Clause 18: The tracking system of clause 1, wherein the shield is coupled to the second connector such that it circumferentially surrounds the opening.

Clause 19: A tracking system including a first connector having a needle extending from the first connector and a needle guard circumferentially surrounding the needle, a second connector removably coupled to the first connector, the second connector having an opening configured to receive the needle when the first connector is coupled to the second connector, a wireless transmitter disposed on one of the first connector and the second connector, the wireless transmitter configured to wirelessly communicate with an external device, and a shield coupled to one of the first connector and the second connector, the shield configured to axially move relative to the wireless transmitter to block and unblock the wireless transmitter, and a tracking device communicatively coupled to the wireless transmitter, wherein the tracking device is configured to detect a status change of the wireless transmitter.

Clause 20: A method of tracking a coupling device, the method including detecting a first status of a wireless transmitter coupled to a coupling device, the first status associated with the coupling device being in an uncoupled configuration and the wireless transmitter being in one of a blocked or an unblocked state, wherein the coupling device includes a first connector coupled to a fluid source and a second connector coupled to a patient, detecting a second status of the wireless transmitter, the second status associated with the coupling device being in a coupled configuration and the wireless transmitter being in the blocked or the unblocked state, wherein the second status is different than the first status, determining a status change of the wireless transmitter when the wireless transmitter transitions the first status to the second status, based on the status change, increase a status change number associated with a total number of status changes detected for the wireless transmitter, compare the status change number to a predetermined threshold, and generate an alert if the status change number exceeds the predetermined threshold.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A tracking system comprising:

a first connector having a needle extending from the first connector and a needle guard circumferentially surrounding the needle;

a second connector removably coupled to the first connector, the second connector having an opening configured to receive the needle when the first connector is coupled to the second connector;

a wireless transmitter disposed on one of the first connector and the second connector, the wireless transmitter configured to wirelessly communicate with an external device;

a tracking device communicatively coupled to the wireless transmitter; and a shield coupled to one of the first connector and the second connector via a biasing element, the shield configured to axially move relative to the wireless transmitter to block and unblock the wireless transmitter.

2. The tracking system of claim 1, wherein the biasing element has a compressed state and an expanded state, the shield being in a compressed state when the biasing element is in the compressed state and the shield being in an extended state when the biasing element is in the expanded state.

3. The tracking system of claim 1, wherein the biasing element causes axial movement of the shield relative to the first connector.

4. The tracking system of claim 1, wherein the biasing element causes axial movement of the shield relative to the second connector.

5. The tracking system of claim 1:

wherein the tracking device is configured to transmit a signal to the wireless transmitter and receive a response signal from the wireless transmitter in response to the signal.

6. The tracking system of claim 1, wherein the tracking device is disposed proximate the wireless transmitter.

7. The tracking system of claim 1, wherein the tracking device is configured to track a status change of the wireless transmitter.

8. The tracking system of claim 7, wherein the status change includes one of the wireless transmitter transitioning from a blocked state to an unblocked state and the wireless transmitter transitioning from the unblocked state to the blocked state.

9. The tracking system of claim 1 further comprising:

a flow control device coupled to the second connector via a delivery line and configured to control a flow of fluid within the delivery line, the flow control device including the tracking device, wherein the tracking device is configured to transmit a signal to the wireless transmitter and receive a response signal from the wireless transmitter in response to the signal.

10. The tracking system of claim 1, wherein the shield includes a leg extending from the shield, the leg and the shield configured to move upon application of a force.

11. The tracking system of claim 1, wherein the shield covers and blocks the wireless transmitter when the first connector is decoupled from the second connector.

12. The tracking system of claim 1, wherein the shield uncovers the wireless transmitter when the first connector is coupled to the second connector.

13. The tracking system of claim 1, wherein the shield uncovers the wireless transmitter when the first connector is decoupled from the second connector.

14. The tracking system of claim 1, wherein the shield blocks and covers the wireless transmitter when the first connector is coupled to the second connector.

15. The tracking system of claim 1, wherein the shield is coupled to the first connector such that it circumferentially surrounds the needle guard and the needle.

16. The tracking system of claim 1, wherein the shield is coupled to the second connector such that it circumferentially surrounds the opening.

17. A tracking system comprising:

a first connector having a needle extending from the first connector and a needle guard circumferentially surrounding the needle;

a second connector removably coupled to the first connector, the second connector having an opening configured to receive the needle when the first connector is coupled to the second connector;

a wireless transmitter disposed on one of the first connector and the second connector, the wireless transmitter configured to wirelessly communicate with an external device;

a shield coupled to one of the first connector and the second connector, comprising a leg extending from the shield, wherein, upon application of a force, the shield and the leg are configured to axially move relative to the wireless transmitter to block and unblock the wireless transmitter; and a tracking device communicatively coupled to the wireless transmitter, wherein the tracking device is configured to detect a status change of the wireless transmitter.

18. A method of tracking a coupling device, the method comprising:

detecting a first status of a wireless transmitter coupled to the coupling device, the coupling device comprising a first connector coupled to a fluid source, a second connector coupled to a patient, and a shield coupled to the first connector or the second connector, wherein the first status is associated with the coupling device being in an uncoupled configuration and the wireless transmitter being in a blocked state, wherein the shield blocks the wireless transmitter when the coupling device is in the uncoupled configuration;

detecting a second status of the wireless transmitter, wherein the second status is different from the first status and associated with the coupling device being in a coupled configuration and the wireless transmitter being in an unblocked state, wherein the shield uncovers the wireless transmitter when the coupling device is in the coupled configuration;

determining a status change of the wireless transmitter when the wireless transmitter transitions from the first status to the second status;

based on the status change, increasing a status change number associated with a total number of status changes detected for the wireless transmitter;

comparing the status change number to a predetermined threshold; and generating an alert if the status change number exceeds the predetermined threshold.

19. The tracking system of claim 17, wherein the shield includes a biasing element having a compressed state and an expanded state, the shield is in a compressed state when the biasing element is in the compressed state, and the shield is in an extended state when the biasing element is in the expanded state.

20. The tracking system of claim 19, wherein the biasing element causes axial movement of the shield relative to one of the first connector and the second connector such that the shield is in a compressed state when the biasing element is in the compressed state and in an extended state when the biasing element is in the expanded state.

* * * * *